United States Patent
Wauchop (10) Patent No.: US 10,502,921 B1
(45) Date of Patent: Dec. 10, 2019

(54) ATTACHABLE LIGHT FILTER FOR PORTABLE ELECTRONIC DEVICE CAMERA

(71) Applicant: T. Simon Wauchop, Aurora (CA)

(72) Inventor: T. Simon Wauchop, Aurora (CA)

( * ) Notice: Subject to any disclaimer, the term of this patent is extended or adjusted under 35 U.S.C. 154(b) by 0 days.

(21) Appl. No.: 16/119,627

(22) Filed: Aug. 31, 2018

Related U.S. Application Data (60) Provisional application No. 62/531,619, filed on Jul. 12, 2017.

(51) Int. Cl.
*G02B 7/00* (2006.01)
*A61B 5/00* (2006.01)
*H04N 5/225* (2006.01)

(52) U.S. Cl.
CPC .............. *G02B 7/006* (2013.01); *A61B 5/445* (2013.01); *H04N 5/2254* (2013.01)

(58) Field of Classification Search
CPC ........ G02B 7/006; G02B 13/001; G02B 5/20; G02B 7/003; G02B 7/14; G02B 13/003; H04N 5/2254; A61B 5/445
See application file for complete search history.

(56) References Cited

U.S. PATENT DOCUMENTS

| | | | |
|---|---|---|---|
| 8,543,519 B2 | 9/2013 | Guyon et al. | |
| 2011/0294543 A1 | 12/2011 | Lapstun et al. | |
| 2013/0107109 A1* | 5/2013 | Yang ..................... | G06F 1/1632 348/373 |
| 2013/0225969 A1 | 8/2013 | Bao et al. | |
| 2014/0092238 A1 | 4/2014 | Sandhu et al. | |
| 2014/0285812 A1 | 9/2014 | Levitz | |
| 2015/0042877 A1* | 2/2015 | O'Neill ................ | H04N 5/2254 348/376 |
| 2016/0035109 A1 | 2/2016 | Kikuchi et al. | |
| 2016/0040978 A1 | 2/2016 | Boppart et al. | |
| 2016/0166194 A1 | 6/2016 | Gareau et al. | |
| 2017/0153408 A1* | 6/2017 | Clark ..................... | G02B 7/006 |

\* cited by examiner

*Primary Examiner* — Jade R Chwasz
(74) *Attorney, Agent, or Firm* — Cramer Patent & Design, PLLC; Aaron R. Cramer (57) ABSTRACT

A light filter device is capable of removable attachment to a portable electronic device. The light filter device transmits modified images of human skin into the mobile telephone displaying the same in a format suitable for analysis relating to skin conditions and diseases. The light filter device includes a first section, a second section being a mirror image of the first section, a protective filter housing affixed to a first section upper surface, a filter selector tab extending outward through a groove which is centrally located along a first side of the protective filter housing, a first filter cover having an aperture aligned with the first filter cover, the filter carrier, and the second filter cover, and a first adjustment knob and a second adjustment knob.

13 Claims, 7 Drawing Sheets

ATTACHABLE LIGHT FILTER FOR PORTABLE ELECTRONIC DEVICE CAMERA

RELATED APPLICATIONS

The present invention was first described in and claims the benefit of U.S. Provisional Patent Application No. 62/531,619 filed on Jul. 12, 2017, the entire disclosures of which are incorporated herein by reference.

FIELD OF THE INVENTION

The present invention relates generally to the field of light filters and more specifically relates to an attachable light filter for a mobile telephone camera.

BACKGROUND OF THE INVENTION

Skin cancers, and many other skin diseases such as eczema, shingles etc., may present in a variety of types having varying degrees of seriousness. While many types of skin diseases are not considered life threatening, some forms of melanoma are considered both aggressive and deadly. Additionally, while eczema and shingles are not considered life threatening, they can be extremely painful and debilitating. Therefore, a skin disease screening process which allows for quick and non-invasive assessment of a given skin anomaly is potentially lifesaving or at least quality of life improving.

One technique for assessing potential skin damage is to view a selected region of skin under ultra-violet ("UV"), covering the wavelength range from two hundred and ninety-two to four hundred nanometers (292-400 nm) or infrared ("IR"), covering the light range from roughly seven hundred nanometers to one millimeter (700 nm to 1 mm) photo imaging. This technique permits portions of the selected region of skin to be viewed for sun damage, melanomas, eczemas, shingles etc., which may not be readily apparent with the naked eye.

Most forms of UV and IR photography involve expensive cameras and associated equipment therefore a less expensive method which utilizes the camera feature typically found on modern mobile phones is desired. Among these are found in: U.S. Pat. App. Pub. Nos. 2016/0166194; 2016/0040978; and 2014/0285812. These prior art references are representative of devices which interact with the camera of a mobile telephone to assist in the detection of skin disease.

However, none of the above inventions and patents, taken either singly or in combination, is seen to describe the invention as claimed. Thus, a need exists for a method to utilize the camera of a mobile telephone to detect skin anomalies including melanoma and a wide variety of other diseases in a manner which is simple and cost-effective. The attachable light filter for a mobile telephone camera accomplishes this task.

SUMMARY OF THE INVENTION

In view of the foregoing disadvantages inherent in the prior art, it has been observed that there is need for an attachable light filter for a mobile telephone camera.

To achieve the above and other objectives, the present invention provides for a light filter device removably secured about a portable electronic device with a lens for a camera, comprising a clamp having a first section removably secured to a second section of the clamp and a protective filter housing affixed to the first section of the clamp. The first section of the clamp includes a pass-through first filter and a pass-through second filter. The protective filter housing includes a first housing is affixed to a second housing that captures a filter carrier which holds the first filter and the second filter. The first filter and the second filter are selectable by actuation of a filter selector tab that travels along a travel path within a groove disposed partially circumferentially within the protective filter housing along one side of the protective filter housing. The interior of the groove terminates at each end with a groove stop, thereby limiting the movement of the filter selector tab.

The pass-through first filter may be an ultraviolet filter which may only permit ultraviolet light to pass through. The pass-through second filter is an infrared filter which may only permit infrared light pass through. The clamp may be generally C-shaped.

In a separate embodiment, the light filter device may be removably secured about a portable electronic device with a lens for a camera and comprise a first section which has a pair of first section side surfaces, a first section upper surface, a first section lower surface, a first section front surface, a first section inner surface, and a first section rear surface. It may also comprise a second section being a mirror image of the first section with the length of the first section upper surface and the first section lower surface being greater than the length of the second section upper surface and the second section lower surface. The second section may have a pair of second section side surfaces, a second section upper surface, a second section lower surface, a second section front surface, a second section inner surface, and a second section rear surface, the first section inner surface and the second section inner surface contact a perimeter edge of the portable electronic device located closest to the lens. The device also comprises a protective filter housing affixed to the first section upper surface, the length of the first section upper surface and the first section lower surface aligns a first filter and a second filter, upon manipulation thereof with the lens of the portable electronic device, the protective filter housing and the first section is installed over the lens, the protective filter housing includes the first housing affixed to the second housing that captures the filter carrier which holds the first filter and the second filter.

The device also comprises a filter selector tab extends outward through a groove which is centrally located along a first side of the protective filter housing. The filter selector tab has a travel path that is arcuate, and movement of the filter carrier is rotational relative to a first housing and a second housing. The filter selector tab also is affixed to a filter carrier, the filter carrier is movable relative to the housings via manipulation of the filter selector tab within the groove between a pair of groove stops. A first one of the groove stops is located at a first filter position and a second one of the groove stops is located at a second filter position.

The device also comprises a first filter cover which has an aperture which is aligned with the first filter cover, the filter carrier, and the second filter cover and a first adjustment knob and a second adjustment knob. The second adjustment knob is adjacent to the first adjustment knob. Each of the adjustment knobs are secured to an individual adjustment pin having an adjustment pin first end and an adjustment pin second end. Furthermore, each of the adjustment pins threadingly engage and secure the first section to the second section.

The width between the first section and the second section may be increased by turning both the first adjustment knob and the second adjustment knob in a common first direction or decreased by turning both the first adjustment knob and the second adjustment knob in a common second direction. The adjustable distance between the first section and the second section permits the light filter device to be secured about various portable electronic devices of varying widths. The first filter position indicates the material corresponding to the first filter and the second filter position indicates the type of material corresponding to the second filter.

The first section may be generally L-shaped while the second section may also be generally L-shaped. The filter selector tab may be manipulated against the second one of the groove stops and the second filter is aligned with the first filter cover, the aperture, the second filter cover, and the lens of the portable electronic device.

The first filter cover may include a translucent material permitting light reflected from a given subject to pass firstly through the first filter cover, secondly through a properly aligned pass-through filter, thirdly through the aperture, fourthly through the second filter cover and into a properly aligned lens of the portable electronic device to which the light filter device is secured. The first aperture is sized so as to be as wide as the first filter cover or the second filter cover to enable as much leeway in positioning of the light filter device over the lens of a portable electronic device.

The filter carrier may selectively carry and position the first filter and the second filter while the second filter cover may include a similar material as the first filter cover. The first filter and the second filter may be located within the filter carrier, which is wholly encompassed between the first housing and the second housing. The first housing, the second housing, and the filter carrier may be circular in cross-section. The device may also comprise software readily available on the portable electronic device with the camera that will photograph and store and view images taken through the light filter device utilizing either the first filter or the second filter.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY 10 light filter device
15 portable electronic device
16 portable electronic device lens
20 first section
25 second section
26a first section upper surface
26b second section upper surface
27a first section lower surface
27b second section lower surface
28a first section front surface
28b second section front surface
28c first section inner surface
28d second section inner surface
29a first section side surface
29b second section side surface
29c first section rear surface
29d second section rear surface
30 filter selector tab
35 first filter position
36 first filter
40 second filter position
41 second filter
45 travel path
46 filter carrier
50 groove
51 groove stop
55 protective filter housing
56 first housing
57 second housing
60 first protective filter cover
61 aperture
65 first adjustment knob
70 second adjustment knob
75 adjustment pin
80 second protective filter cover

DESCRIPTION OF THE INVENTION

Figure 1:
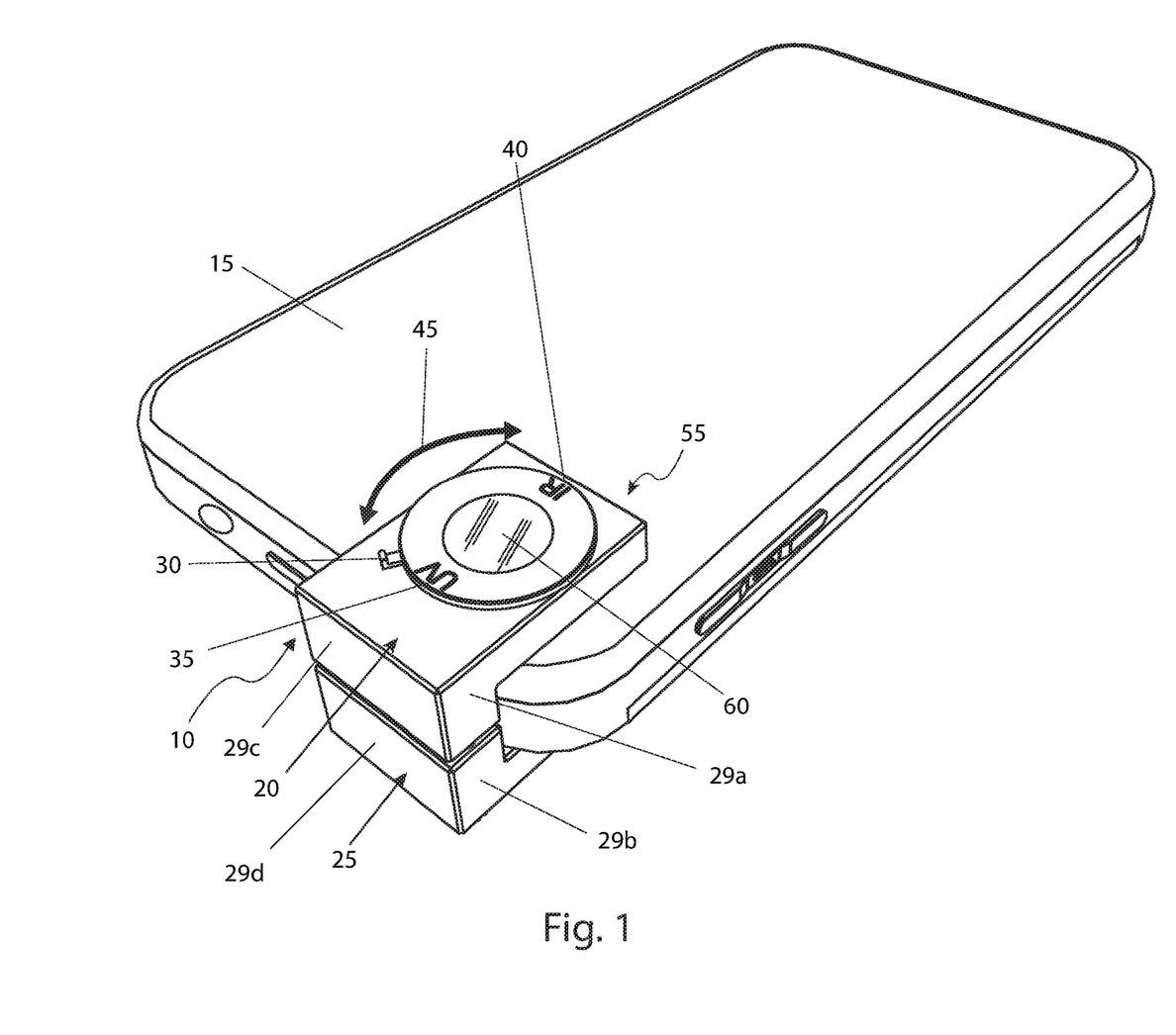
FIG. 1 is an environmental top perspective view of a light filter device 10 as installed on a portable electronic device 15, according to an embodiment of the present invention.
Figure 2:
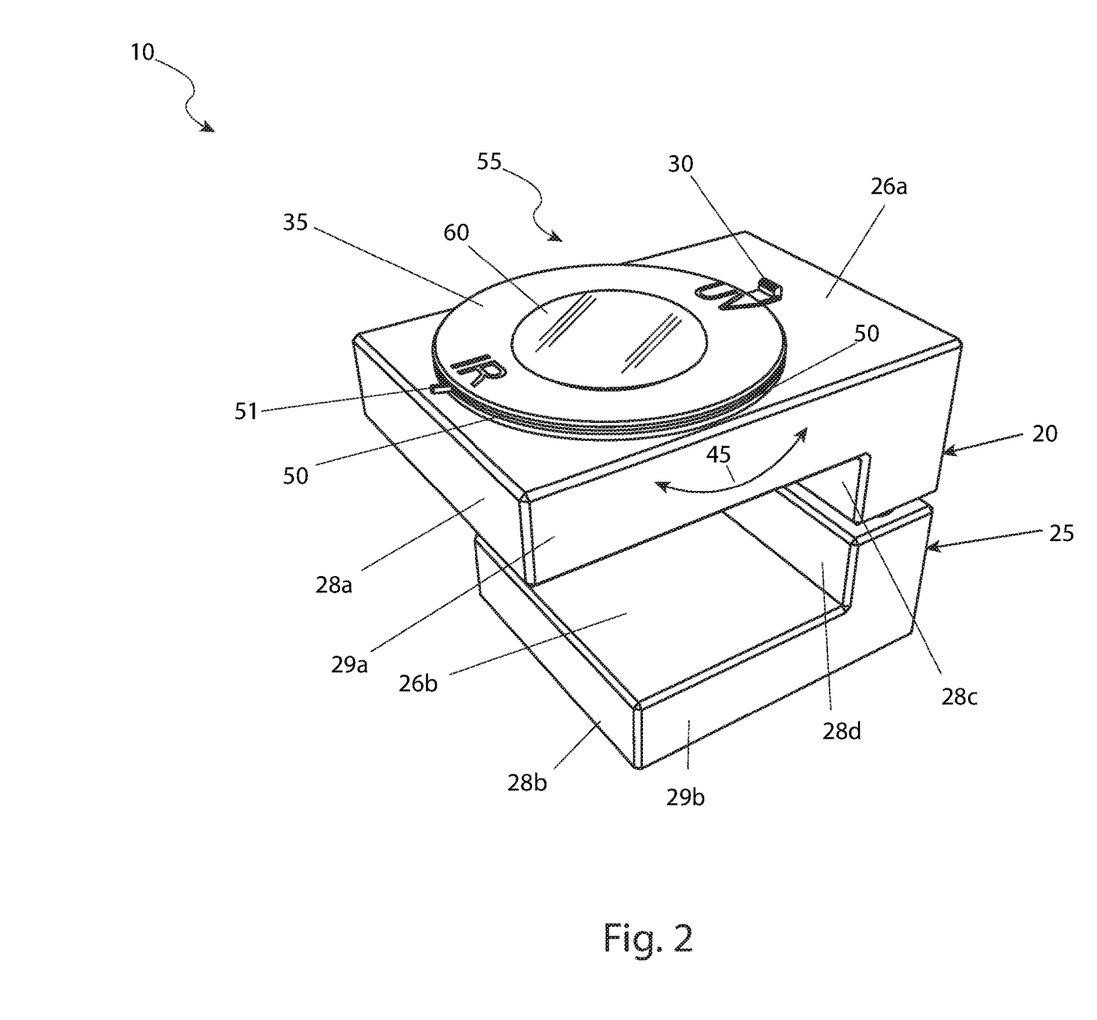
FIG. 2 is an environmental top perspective view of a light filter device 10 opposite of the view of FIG. 1, according to an embodiment of the present invention.

The present invention is directed to a light filter device 10. Referring now to the drawings, there is shown in FIG. 1 an environmental top perspective view of a light filter device (herein described as the "device") 10, according to an embodiment of the present invention, capable of being removably secured about a portable electronic device 15 having a lens 16 for a camera. FIG. 2 depicts a reverse perspective view of the device 10 removed from the portable electronic device 15. The light filter device 10, comprises a generally "C"-shaped clamp having a first section 20 removably secured to a device second section 25. A protective filter housing 55 is affixed to, or a portion of, the first section 20 and includes a pass-through first filter 36 (such as an ultraviolet (UV) filter, meaning only UV light may pass through) and a pass-through second filter 41 (such as an infrared (IR) filter, meaning only IR light may pass through). The protective filter housing 55 is preferably comprised of a first housing 56 affixed or attached to a second housing 57 that captures a filter carrier 46 which holds each filter 36, 41. Each filter 36, 41 is selectable by actuation of a filter selector tab 30 that travels along a travel path 45 within a groove 50 disposed partially circumferentially within the protective filter housing 55 along one (1) side of the protective filter housing 55. The interior of the groove 50 terminates at each end with a groove stop 51, thereby limiting the movement of the filter selector tab 30.

Figure 3:
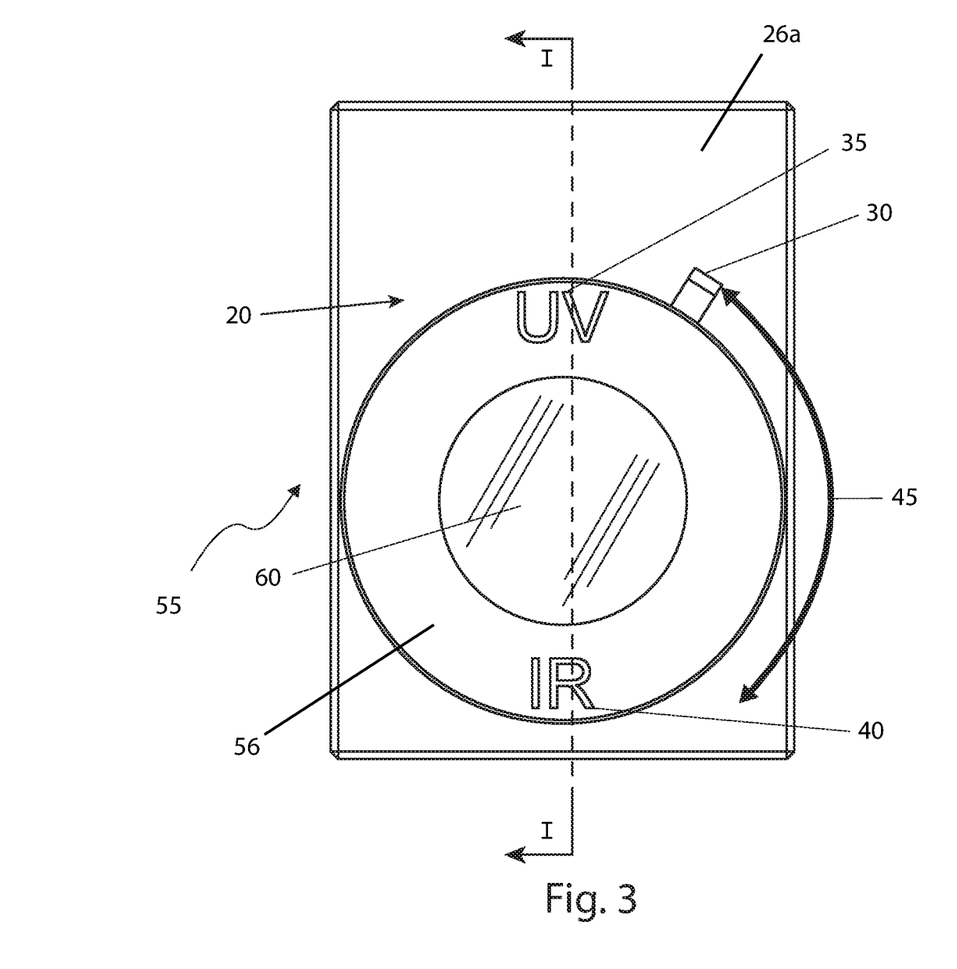
FIG. 3 is front view of a light filter device 10, according to an embodiment of the present invention.

Referring now to FIG. 3, a front view of the device 10, according to an embodiment of the present invention, shows the first section 20, the filter selector tab 30, the first position 35, the second position 40, the travel path 45, the protective filter housing 55, and the first filter cover 60. The first section 20 is generally "L"-shaped, having a pair of first section side surfaces 29c, a first section upper surface 26a, a first section lower surface 27a, a first section front surface 28a, a first section inner surface 28c, and a first section rear surface 29a. The second section 25 is also generally "L"-shaped, having a pair of second section side surfaces 29d, a second section upper surface 26b, a second section lower surface 27b, a second section front surface 28b, a second section inner surface 28d, and a second section rear surface 29b. The second section 25 is substantially a mirror image of the first section 20, except that the length of the first section upper surface 26a and first section lower surface 27a is greater than the length of the second section upper surface 26b and second section lower surface 27b. The first section inner surface 28c and second section inner surface 28d are adapted to contact the perimeter edge of the portable electronic device 15 located closest to the lens 16. The protective filter housing 55 is affixed to or integral with the first section upper surface 26a. The length of the first section upper surface 26a and first section lower surface 27a is such that it aligns the first filter 36 and second filter 41, upon manipulation thereof, with the lens 16 of the portable electronic device 15.

Figure 4:
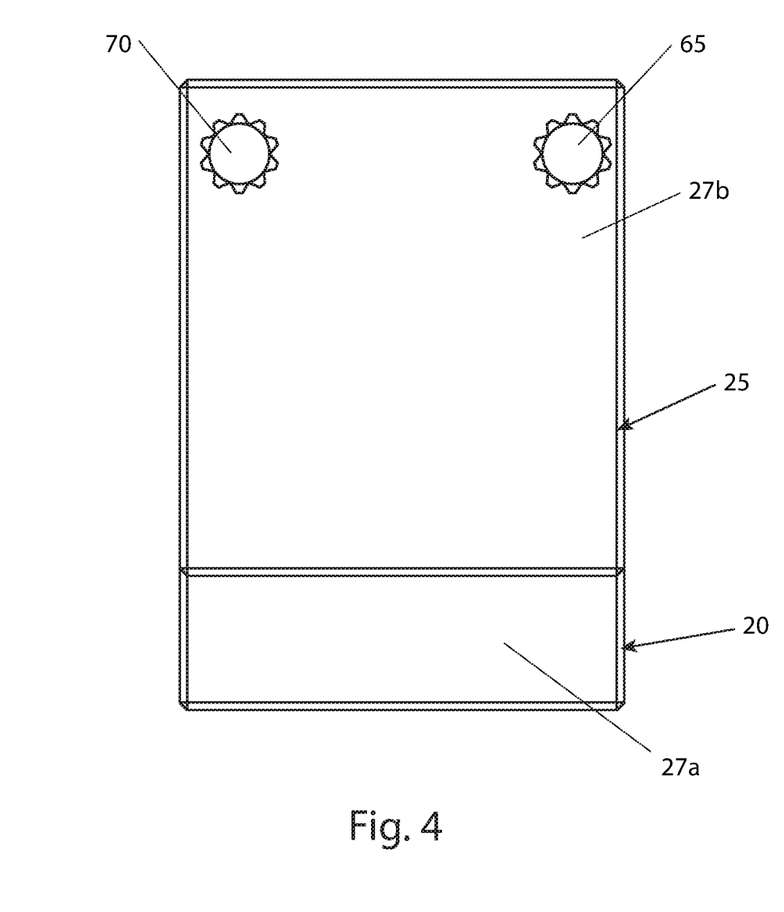
FIG. 4 is a rear view of a light filter device 10, according to an embodiment of the present invention.

Referring now to FIG. 4, a rear view of the device 10, according to an embodiment of the present invention, shows the first section 20, the second section 25, a first adjustment knob 65, and a second adjustment knob 70 adjacent the first adjustment knob 65. Each adjustment knob 65, 70 is secured to an individual adjustment pin 75 having an adjustment pin first end and an adjustment pin second end (see FIG. 5). Each adjustment pin 75 is ideally configured to threadingly engage and secure the first section 20 to the second section 25. The width between the first section 20 and the second section 25 may be increased by turning both the first adjustment knob 65 and the second adjustment knob 70 in a common first direction or decreased by turning both the first adjustment knob 65 and the second adjustment knob 70 in a common second direction. The adjustable distance between the first section 20 and the second section 25 is envisioned to permit the device 10 to be secured about various portable electronic devices 15 of likewise varying widths. It is also envisioned that a single adjustment knob may actuate a single adjustment pin 75 in a similar fashion as described above.

Figure 5:
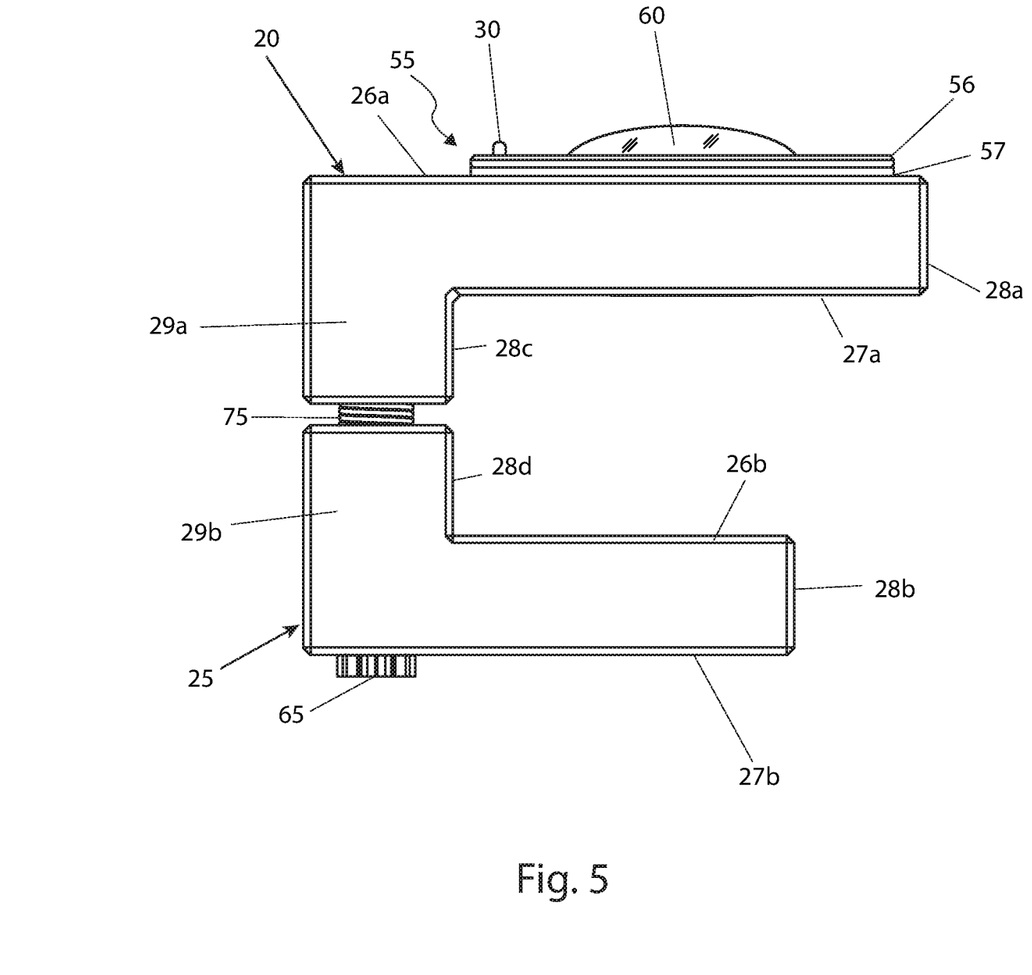
FIG. 5 is a first side view of a light filter device 10, according to an embodiment of the present invention.

Referring now to FIG. 5, a first side view of the device 10, according to an embodiment of the present invention; showing the first section 20 secured to the second section 25 by means of the adjustment pins 75. As noted above with respect to FIG. 4, each adjustment pin 75 may be actuated by movement of the knobs 65, 70 to either lengthen or widen the distance between the first section 20 and the second section 25. FIG. 5 also details the filter selector tab 30, the protective filter housing 55, and the first filter cover 60.

Figure 6:
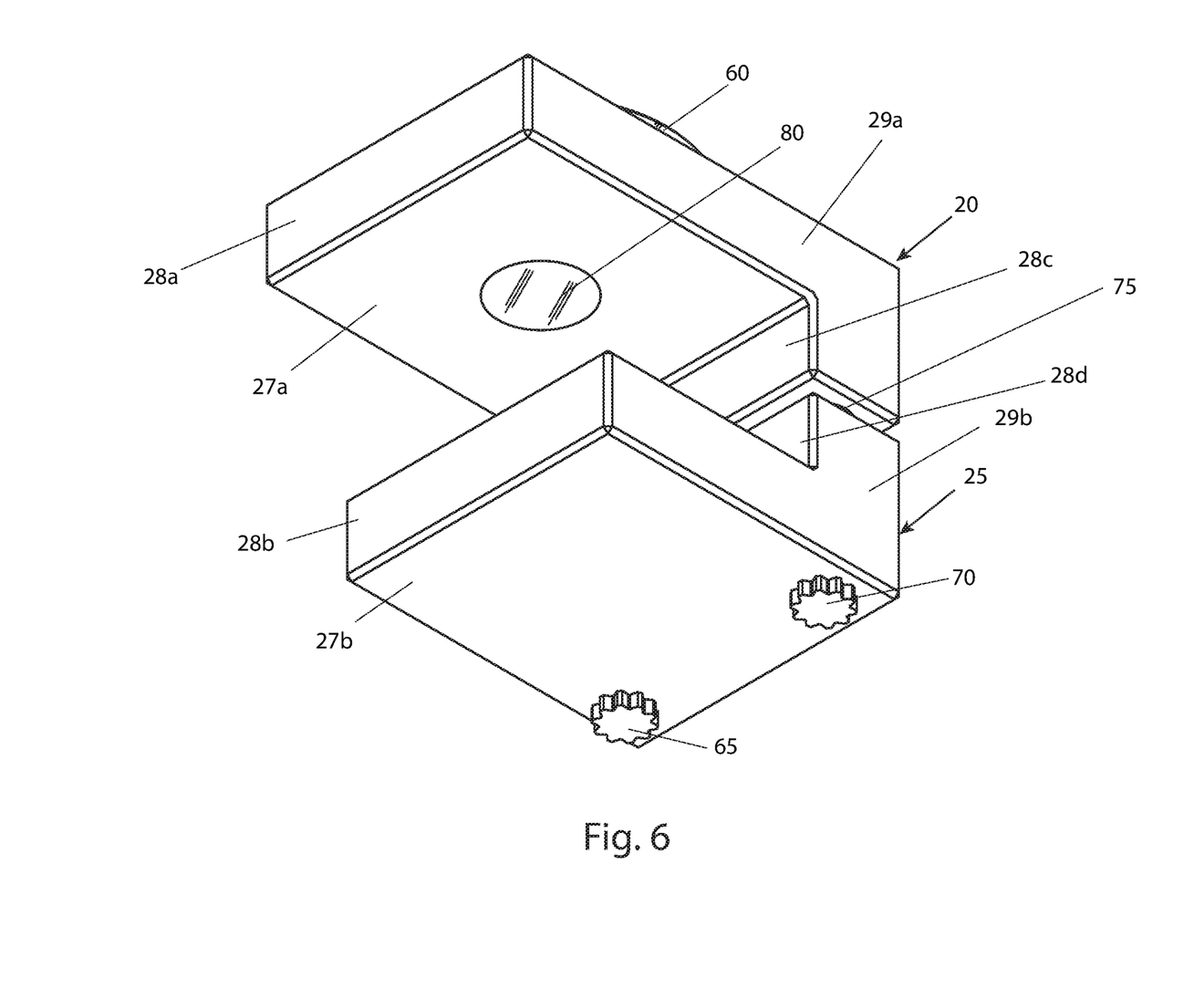
FIG. 6 is a bottom perspective view of a light filter device 10, according to an embodiment of the present invention; and, FIG. 7 is a cut-away view of the light filter device 10 as installed on a portable electronic device 15 along the line I-I (as seen in FIG. 3), according to an embodiment of the present invention.

Referring to FIG. 6, a bottom perspective view of the device 10, according to an embodiment of the present invention; showing the device first section 20 secured to the second section 25 by means of the adjustment pins 75. As noted above with respect to FIGS. 4 and 5, each adjustment pin 75 may be actuated by movement of the knobs 65, 70 to either lengthen or widen the distance between the first section 20 and the second section 25. FIG. 6 also illustrates the protective filter housing 55 and the second filter cover 80 positioned within the first section bottom surface 27a, which is vertically aligned with and opposite the first protective filter cover 60.

Figure 7:
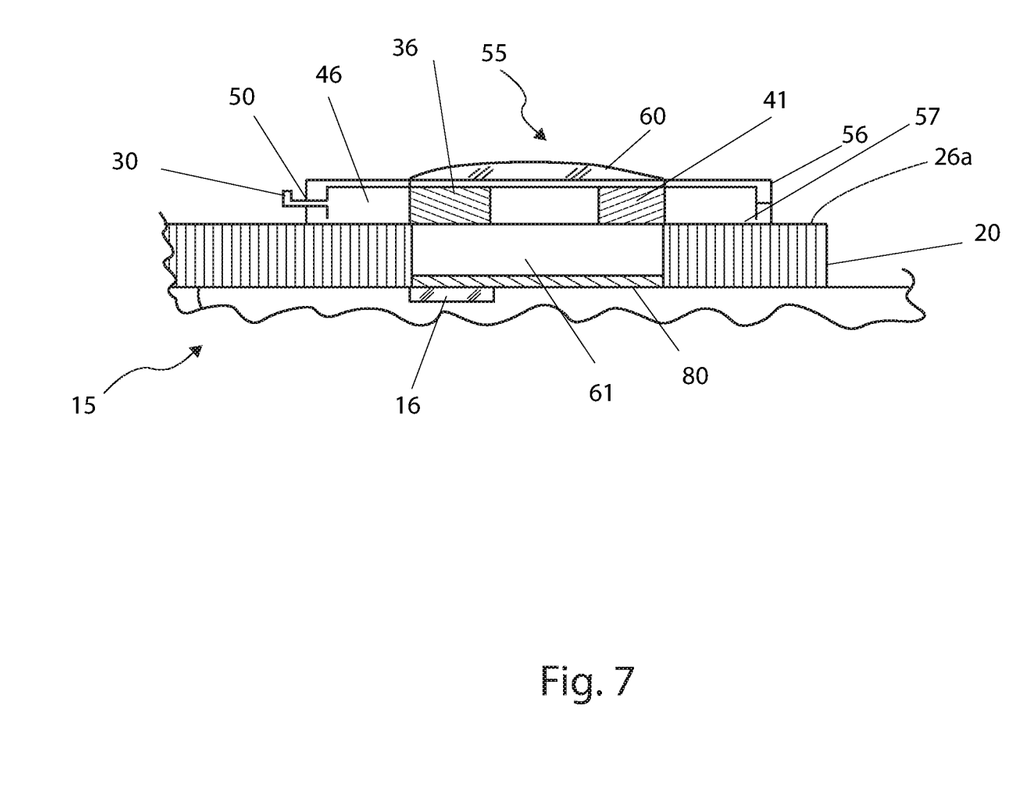

Referring now to FIG. 7, which illustrates a cut-away view of the protective filter housing 55 and first section 20 as the device 10 is installed over a lens 16 of a portable electronic device 15. This illustrates the protective filter cover 55 to be positioned on the first section upper surface 26a. An aperture 61 is aligned with the first filter cover 60, the filter carrier 46 (which selectively carries and positions the first filter 36 and second filter 41), and the second filter cover 80. The aperture 61 is preferably sized so as to be as wide as either or both the first filter cover 60 and second filter cover 80 to enable as much leeway in positioning of the device 10 over the lens 16 of a portable electronic device 10. The first filter cover 60 comprises a translucent material permitting light reflected from a given subject to pass firstly, through the first filter cover 60; secondly through a properly aligned pass-through filter 36 or 41; thirdly, through the aperture 61; fourthly, through a second filter cover 80, and into a properly aligned lens 16 of a portable electronic device 15 to which device 10 is secured. The second filter cover 80 comprises a similar or identical material as the first filter cover 60.

The first filter 36 and second filter 41 are located within a filter carrier 46, which is wholly encompassed between the first housing 56 and second housing 57. In a preferred embodiment, the first housing 56, second housing 57, and filter carrier 46 are circular in cross-section. As such, the travel path 45 of the filter selector tab 30 is arcuate and movement of the filter carrier 46 is rotational relative to the first housing 56 and second housing 57. The filter selector tab 30 is affixed to and operably controls the filter carrier 46 and extends outward through a groove 50 which is centrally located along a first side of the protective filter housing 55. The filter carrier 46 is movable relative to the housings 56, 57 via manipulation of the filter selector tab 30 within the groove 50 between a pair of groove stops 51. A first one (1) of the groove stops 51 is located at a first filter position 35 (identified as indicia located on the upper surface of the first housing 56). Similarly, a second one (1) of the groove stops 51 is located at a second filter position 40 (also identified as indicia located on the upper surface of the first housing 56).

It is envisioned that the first filter position 35 indicates the type of material corresponding to the first filter 36 and that the second filter position 40 indicates the type of material corresponding to the second filter 41. When the filter selector tab 30 is manipulated against the first one (1) of the groove stops 51 (in the exemplary embodiment, aligned with the first filter position 35), the first filter 36 is aligned with the first filter cover 16, aperture 61, second filter cover 80, and lens 16 of the portable electronic device 10. In a similar manner, when the filter selector tab 30 is manipulated against the second one (1) of the groove stops 51 (in the exemplary embodiment, aligned with the second filter position 40), the second filter 41 is aligned with the first filter cover 16, aperture 61, second filter cover 80, and lens 16 of the portable electronic device 10. It is also envisioned that software readily available on typical portable electronic devices 15 having a camera will permit a user to photograph and store and view images taken through the device 10 utilizing either the first filter 36 or second filter 41. It is envisioned this information may then be utilized or interpreted by the user or software on the portable electronic device 15 or both, to assess the presence of various skin diseases such as cancer, eczema, shingles etc.

The exact specifications, materials used, and method of use of device 10 may vary upon manufacturing. The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A light filter device removably secured about a portable electronic device with a lens for a camera, comprising:
   a first section having a pair of first section side surfaces, a first section upper surface,
   a first section lower surface, a first section front surface, a first section inner surface, and a first section rear surface;
   a second section complementary to the first section, the length of the first section upper surface and the first section lower surface is greater than the length of the second section upper surface and the second section lower surface, the second section having a pair of second section side surfaces, a second section upper surface, a second section lower surface, a second section front surface, a second section inner surface, and a second section rear surface, the first section inner surface and the second section inner surface contact a perimeter edge of the portable electronic device located closest to the lens;
   a protective filter housing affixed to the first section upper surface, the length of the first section upper surface and the first section lower surface aligns a first filter and a second filter, upon manipulation thereof with the lens of the portable electronic device, the protective filter housing and the first section is installed over the lens, the protective filter housing includes the first housing affixed to the second housing that captures the filter carrier which holds the first filter and the second filter;
   a filter selector tab extending outward through a groove which is centrally located along a first side of the protective filter housing, the filter selector tab having a travel path that is arcuate and movement of the filter carrier is rotational relative to a first housing and a second housing, the filter selector tab affixed to a filter carrier, the filter carrier is movable relative to the housings via manipulation of the filter selector tab within the groove between a pair of groove stops, a first one of the groove stops is located at a first filter position and a second one of the groove stops is located at a second filter position;
   a first filter cover having an aperture aligned with the first filter cover, the filter carrier, and the second filter cover; and
   a first adjustment knob and a second adjustment knob, the second adjustment knob adjacent to the first adjustment knob, each of the adjustment knobs are secured to an individual adjustment pin having an adjustment pin first end and an adjustment pin second end, each of the adjustment pins threadingly engage and secure the first section to the second section.

2. The light filter device according to claim 1, wherein the width between the first section and the second section are increased by turning both the first adjustment knob and the second adjustment knob in a common first direction or decreased by turning both the first adjustment knob and the second adjustment knob in a common second direction.

3. The light filter device according to claim 2, wherein the adjustable distance between the first section and the second section permits the light filter device to be secured about various portable electronic devices of varying widths.

4. The light filter device according to claim 3, wherein the first filter position indicates the material corresponding to the first filter and the second filter position indicates the type of material corresponding to the second filter.

5. The light filter device according to claim 1, wherein the first section is generally L-shaped.

6. The light filter device according to claim 1, wherein the second section is generally L-shaped.

7. The light filter device according to claim 1, wherein the filter selector tab is manipulated against the second one of the groove stops and the second filter is aligned with the first filter cover, the aperture, the second filter cover, and the lens of the portable electronic device.

8. The light filter device according to claim 1, wherein the first filter cover includes a translucent material permitting light reflected from a given subject to pass firstly through the first filter cover, secondly through a properly aligned pass-through filter, thirdly through the aperture, fourthly through the second filter cover and into a properly aligned lens of the portable electronic device to which the light filter device is secured.

9. The light filter device according to claim 1, wherein the aperture is sized so as to be as wide as the first filter cover or the second filter cover to enable leeway in positioning of the light filter device over the lens of a portable electronic device.

10. The light filter device according to claim 1, wherein the filter earner selectively carries and positions the first filter and the second filter.

11. The light filter device according to claim 1, wherein the second filter cover includes a similar material as the first filter cover.

12. The light filter device according to claim 1, wherein the first filter and the second filter are located within the filter carrier, which is wholly encompassed between the first housing and the second housing.

13. The light filter device according to claim 1, wherein the first housing, the second housing, and the filter carrier are circular in cross-section.

* * * * *